United States Patent [19]

Ostertag et al.

[11] Patent Number: 4,978,394
[45] Date of Patent: Dec. 18, 1990

[54] METAL OXIDE COATED ALUMINUM PIGMENTS

[75] Inventors: Werner Ostertag, Gruenstadt; Norbert Mronga, Dossenheim, both of Fed. Rep. of Germany

[73] Assignee: BASF Aktiengesellschaft, Ludwigshafen, Fed. Rep. of Germany

[21] Appl. No.: 338,107

[22] Filed: Apr. 14, 1989

[30] Foreign Application Priority Data

Apr. 21, 1988 [DE] Fed. Rep. of Germany ....... 3813335

[51] Int. Cl.$^5$ ............................ C09C 1/14; C09C 1/62
[52] U.S. Cl. .................................... 106/404; 106/415; 106/432; 106/436
[58] Field of Search ................ 106/404, 436, 432, 415

[56] References Cited

U.S. PATENT DOCUMENTS 2,886,459 5/1959 Lajoie .
3,440,075 4/1969 Marshall .............................. 106/415
3,582,382 6/1971 Watanabe et al. .................. 106/415
3,718,494 2/1973 Jacobson ............................. 106/415
3,840,381 10/1974 Watanabe ............................ 106/415
3,869,298 3/1975 Suzuki et al. ....................... 106/415
4,076,551 2/1978 Bernhard et al. ................... 106/415
4,840,668 6/1989 Gawol et al. ....................... 106/404

FOREIGN PATENT DOCUMENTS 0133644 3/1985 European Pat. Off. ............ 106/404
7039101 3/1982 Japan .................................. 106/404
3144106 6/1988 Japan .................................. 106/436

Primary Examiner—Paul Lieberman
Assistant Examiner—John Boyd
Attorney, Agent, or Firm—Keil & Weinkauf

[57] ABSTRACT

Metallically bright reflection pigments comprising a substrate of plateletlike aluminum and coatings of titanium oxides applied on top of the substrate are used for coloring paints, plastics, printing inks, ceramic articles, glasses and cosmetic products.

9 Claims, No Drawings

METAL OXIDE COATED ALUMINUM PIGMENTS

The present invention relates to titanium oxide coated aluminum pigments and to the preparation and use thereof.

These metallically bright reflection pigments are part of the group of effect pigments. Effect pigments are plateletlike pigments whose optical effect, if they are applied in oriented form, is angle dependent. Effect pigments find application in high grade coatings, for example automotive coatings, plastics, decorative cosmetics, printing and ceramics.

The pigments according to the invention are more particularly metallic interference/reflection pigments, ie. pigments consisting of a substrate that gives mirror reflection and a coating that produces interference colors.

The number of metallic interference/reflection pigments known at present is small.

They include the classic copper and brass pigments which, by controlled oxidation at the surface, have been adjusted to a certain tarnish color. The interference capable coating forming on the surface of such copper and brass pigments always consists of the oxides of the respective metallic substrate.

EP-A-33,457 describes metallic interference/reconsisting pigments consisting of an $Fe_2O_3$ coated Al substrate. In this case, the interference capable coating does not consist of the oxide of the metallic substrate. The pigments are produced by controlled burning of iron pentacarbonyl in a fluidized bed of hot Al platelets, and depending on the thickness of the $Fe_2O_3$ coating they give yellow, orange, red or violet interference colors.

With every existing metallic interference/reflection pigment the oxidic surface coating is colored. This means, however, that the color effect created by such pigments is not due to interference alone but also due to absorption. The effect is always the result of an interaction between absorption and interference color.

As far as the color brilliance is concerned, this can be an advantage or a disadvantage. The highest color brilliance is observed with those pigments whose layer thickness dependent interference color is close to the absorption color of the oxidic coating. For example, red $Fe_2O_3$ coated Al pigments (red interference color +red absorption color) are very brilliant. Low brilliances are possessed by pigments whose interference color is remote from the absorption color. For example, $Fe_2O_3$ coated Al pigments which, as a result of their layer thickness, have a blue interference color, are brownish gray and dull. In this case, interaction of blue interference color and red absorption color leads to reduced color brilliance.

Since all prior art metallic interference/reflection pigments have, on account of the coloredness of the oxidic coating, a region where their color brilliance is impaired, it will be readily understood that it is of interest for those skilled in pigments to develop metallic interference/reflection pigments whose coating thickness can be varied without the brilliance of the respective interference color being impaired by the absorption color of the coating.

It is an object of the present invention to develop metallic interference/reflection pigments where a metallic substrate has been provided with a non-absorbing interference capable coating. As a minimum, the pigments should have a structure such that any absorption by the coating(s) does not impair the brilliance of interference.

We have found that this object is achieved by coating plateletlike aluminum pigment with filmlike coatings of titanium oxides of different thicknesses. These titanium oxide coated aluminum pigments can be additionally coated with chromium(III) oxide hydrate (non-interfering in the greenish blue region) or with $Fe_2O_3$ (non-interfering in the yellowish red region).

The aluminum pigments according to the invention can be prepared by the chemical vapor deposition (CVD) process. In this process, $TiCl_4$ vapor is reacted in low concentration with $H_2O$ vapor in a fluidized bed in the presence of hot moving Al particles. The highly simplified overall equation reads as follows:

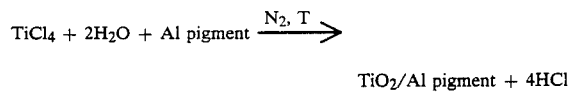

$$TiCl_4 + 2H_2O + Al\ pigment \xrightarrow{N_2,\ T} TiO_2/Al\ pigment + 4HCl$$

This makes it possible to produce metallically bright pigments that show interference colors.

The Al substrate can take the form of Al platelets die punched from Al foil or of Al pigments produced using existing atomizing and milling techniques. The desired particle size range is from 10 to 120 μm for the median diameter of the platelets. The specific free surface area (BET) of the Al starting pigment is from 0.5 to 5 m²/g.

The platelet surface should be substantially free of oils, greases or other coating agents. Commercial products may be used.

In detail, plateletlike Al pigment is coated with $TiO_2$ by introducing dry Al pigment into a heatable fluidized bed reactor made of metal or glass and is made to fluidize with inert fluidizing gas which, for safety reasons, may contain an admixture of not more than 5% by volume of oxygen. To avoid the carryout of fine particles, the fluidized bed reactor advantageously has a filter at the top end.

The fluidizable material is heated to from 100 to 400° C. by wall or radiative heating. Particularly advantageous reaction temperatures are the range from 180 to 250° C. To prevent electrostatic charge buildup, steam is introduced into the fluidized bed during the heating up phase. This is advantageously effected by passing the fluidizing gas, or a portion thereof, through hot water, so that the fluidizing gas becomes laden with $H_2O$ vapor. However, steam may also be introduced into the fluidized bed by way of a nozzle mounted at the side of the fluidized bed reactor. Once the desired fluidized bed end temperature has been reached, TiCl vapor is passed into the fluidized bed by way of a further nozzle mounted at the side of the fluidized bed. Advantageously this is done by loading an inert carrier gas, for example Nz, with the desired amount of $TiCl_4$.

To form qualitatively high grade, ie. uniform, filmlike $TiO_2$ coatings on the surface of the Al particles, it is important that TiCl be introduced into the fluidized bed only in low concentration. In the fluidized bed, it can then react with the water vapor present there in excess.

Tests have shown that, based on the total amount of the other gases or vapors introduced into the fluidized bed, the $TiCl_4$ vapor concentration must not exceed 5% by volume.

This figure must be viewed against the fact that $H_2O$ vapor is always present at more than 2 moles/1 mole of $TiCl_4$ and is included in the total amount of other gases.

As the reaction progresses, the Al platelets become coated with a thicker and thicker TiO$_2$ coating. The TiO$_2$ coated Al pigments first show a bluish color and then a yellow, gold, red, violet, green, blue to yellow color. The gas phase chemical vapor deposition coating process is advantageously operated as a batchwise process. Once the desired interference color has been obtained, the TiCl$_4$ supply is discontinued, and the fluidized bed is cooled down and discharged. The HCl which forms in the course of the reaction leaves the reactor in the vapor form on the off-gas side for straightforward waste disposal.

The characterization of the interference/reflection pigment produced by the above-described process reveals very homogeneous and extremely uniform TiO$_2$ coatings on the Al substrates. The surface of the coating is smooth. The coating itself consists of dense polycrystalline TiO$_2$. There is no indication of any crystallographic preference orientation. The pigments show a very high degree of metallic brightness. Their color depends on the layer thickness.

The color effect produced by the interference pigments described is intensifiable by various additional measures. As is known, the color effect of interference colors can be enhanced if it is possible to lower or reduce the white content of the light. This is possible by partially reducing the TiO$_2$ coating to give, besides unchanged TiO$_2$, titanium oxides where the titanium is in an oxidation state <4, for example dark TiO, or perhaps TiN. The partial reduction of the TiO$_2$ coating of the TiO$_2$ coated Al pigments can be effected with H$_2$, CO, hydrocarbons or in particular ammonia at from 400° to 900° C.

A particularly effective measure is the reduction with ammonia at from 400° to 660° C. In this reduction, the flow velocity of the reducing gas should not drop below 0.5 cm/sec. In addition, the reducing gas must be dry. The reduction is advantageously performed by bringing a moving bed of the pigment to be treated into contact with the reducing gas, for example inside a rotating tube or a rotating drum with trip stages, or inside a fluidized bed reactor. The reduction time is from 30 to 360 minutes. As the reduction progresses, the treated material becomes darker and darker, which is due to an increasing proportion of TiO or TiN or titanium oxynitrides.

In fact it is possible, by darkening the interference/reflection pigments used as starting material, to make the interference color of the particular starting material more prominent. For instance, a TiO$_2$ coated Al pigment having a blackish blue interference color appears deep blue following a reducing treatment with NH$_3$ at 600° C. over 1 hour.

The color of the aluminum pigments coated with titanium oxides is in some regions of the spectrum also enhanceable by further inorganic coatings. For instance, it is possible to deepen red pigments by a proportional (in relation to the layer thickness) iron red (Fe$_2$O$_3$) coating. It was also found that green pigments can be made more deeply green by a proportional chromium oxide or CrOOH coating. Such additional inorganic coatings have the further advantage of stabilizing the TiO$_2$ coating, which because of its photoactivity is only of limited usefulness for outdoor applications. Also advantageous in this respect are additional coatings of the TiO$_2$/Al pigment with further uncolored oxides such as SiO$_2$, Al$_2$O$_3$ or ZrO$_2$.

Additional coatings can be applied in a conventional manner in an aqueous medium by hydrolysis of the corresponding salt solutions with subsequent washing and drying of the pigments. A more elegant option is the application of further coatings from the gas phase, since this can take place directly following the TiO$_2$ coating, for example in a fluidized bed. Using the readily vaporizable chlorides of silicon and aluminum, it is possible to apply SiO$_2$ and Al$_2$O$_3$ or alternating SiO$_2$/Al$_2$O$_3$ coatings by the same method as the TiO$_2$ coating.

Similarly, an additional iron oxide coating can be advantageously carried out using CVD techniques. To this end, the same fluidized bed reactor is injected without cooling down with iron pentacarbonyl vapor in place of the TiCl$_4$ vapor. The concentration of the iron pentacarbonyl here must not exceed 5% by volume of the total volume of other gases passed into the fluidized bed. Fe(CO)$_5$ vapor reacts in the fluidized bed with oxygen passed over the fluidized bed at above 150° C., preferably at from 180° to 250° C., in accordance with the following overall equation:

$$2Fe(CO)_5 + \frac{13}{2} O_2 + TiO_2/Al \text{ pigment} \xrightarrow{N_2, T}$$

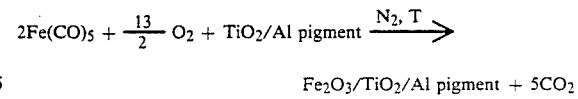

$$Fe_2O_3/TiO_2/Al \text{ pigment} + 5CO_2$$

The thickness of the additional Fe$_2$O$_3$ coating can be controlled via the duration of the reaction time. Even alternating coating with TiO$_2$ and Fe$_2$O$_3$ is possible.

As a statement of principle it must be said that, in the case of additional coatings with the metal oxides mentioned, care must be taken not to change the overall thickness of the envisioned coating if the interference color is not to be changed.

X-ray analysis of alternatingly coated pigments shows TiO$_2$ and Fe$_2$O$_3$ to be present as separate phases. Weathering tests have shown that Fe$_2$O$_3$ coated titanium oxide/aluminum pigments are highly weather resistant, so that their utilizability in outdoor applications, for example for the production of automotive coatings, is ensured.

As well as the coloring of paints, the reflection pigments according to the invention can, however, also be used for coloring plastics, printing inks, ceramic articles, glasses and cosmetic products.

The following experiments illustrate the invention by way of example:

In Examples 1 to 4, the following apparatus was used: infrared heatable fluidized bed reactor made of glass and having a conical fluidizing gas inlet at the bottom and filter socks, cleanable with bursts of nitrogen, at the top; diameter 60 mm, height 1000 mm; two nozzles mounted on the side one third of the way up.

All the reported gas rates refer to 20° C. and 1.013 bar.

EXAMPLE 1

The fluidized bed reactor is charged with 300 g of a commercial aluminum pigment having a BET surface area of 1.5 m$^2$/g and a median particle diameter of 60 1m (90% of the particles are between 35 and 90 um). The pigment is fluidized by blowing 600 l/h of nitrogen and 100 l/h of air into the lower opening of the cone. The air stream is passed through hot water at 50° C. The internal temperature of the fluidized bed is raised to 192°–228° C. by means of the IR radiators. Once that temperature range has been reached, a 300 l/h stream of nitrogen, which has been laden with titanium tetrachloride vapor by being passed through a TiCl₄ filled saturating flask thermostated at 50° C., is blown through a nozzle into the furnace. The titanium tetrachloride reacts with the water vapor introduced with the air stream to give titanium dioxide and hydrogen chloride. Under the chosen reaction conditions, the titanium dioxide formed settles out spontaneously in film form on the aluminum platelets. In total, 400 ml of $TiCl_4$ are introduced into the fluidized bed over a period of 12 hours, a small pigment sample being removed after 50, 100, 150, 170, 190, 210, 230, 250, 270, 290, 310 and 350 ml of TiCl . Yield: 460 g of $TiO_2$ coated aluminum pigment, the titanium level being 28.0% by weight.

To evaluate the color characteristics of the pigment produced according to the invention, 0.4 g of each of the pigment samples is stirred into 3.6 g of a mixed polyester lacquer having a solids content of 21% by weight and dispersed therein for 2 minutes in a Red Devil. Films of the pigmented lacquers are drawn down by means of a wire wound doctor blade (80 μm wet film thickness) on a piece of black and white cardboard. The CIELAB color coordinates are measured with an MCS 111 DATACOLOR spectrophotometer using a GK 111 metallic measuring head at an angle difference of 20° to the gloss angle. The reported color coordinates $L^*$, $a^*$ and $b^*$ relate to standard illuminant D 65, $L^*$ being lightness, $a^*$ denoting the red or green portion and $b^*$ the blue or yellow portion. All the paint films show the high metallic brightness typical of aluminum pigments. In addition they have, as a function of the amount of titanium dioxide applied to the aluminum pigment, pastellike interference colors in the sequence blue, golden, red, violet and green. Interference colors of higher order are obtained from a titanium content of 20% by weight.

EXAMPLE 2

The fluidized bed reactor is charged with 200 g of commercial aluminum pigment having a BET surface area of 1.5 m²/g and a median particle diameter of 60 lm (90% of the particles are between 35 and 90 lm). The pigment is fluidized by blowing in 400 l/h of nitrogen, which has been enriched with water vapor by passage through hot water at 50° C., at the lower opening of the cone. The internal temperature of the fluidized bed is raised to 210°–220° C. by means of the IR radiators. Once this temperature range has been reached, a 150 l/h stream of nitrogen, laden with titanium tetrachloride vapor by passage through a TiCl₄ filled saturating flask thermostated at 50° C., is blown through a nozzle into the furnace. The titanium tetrachloride reacts with the water vapor introduced with the nitrogen stream to give titanium dioxide and hydrogen chloride. Under the chosen reaction conditions the titanium dioxide formed settles out spontaneously in film form on the aluminum platelets. In total, 20 ml of TiCl₄ are introduced into the fluidized bed over a period of 2.5 hours. A drawdown of a pigment sample prepared as described in Example 1 shows high metallic brightness with a blue shimmer.

EXAMPLE 3

The fluidized bed reactor is charged with a mixture of 150 g of commercial aluminum pigment having a BET surface area of 1.5 m²/g and a median particle diameter of 60 μm (90% of the particles being between 35 and 90 μm) and 150 g of commercial aluminum pigment having a BET surface area of 4.5 m²/g and a median particle diameter of 20 μm (90% of the particles being between 6 and 35 μm). The pigment is fluidized and homogenized by blowing 150 l/h of nitrogen and 180 l/h of air in at the lower opening of the cone. The air stream is passed through hot water at 50° C. The internal temperature of the fluidized bed is raised to 195°–200C. by means of the IR radiators. Once this temperature range has been reached, water vapor is introduced into the reactor by means of a 200 l/h nitrogen stream previously passed through hot water at 50° C., and the fluidizing gas stream is loaded with titanium tetrachloride vapor by passage through a TiCl₄ filled saturating flask thermostated at 50° C. Under the chosen reaction conditions, the titanium dioxide formed settles out spontaneously in film form on the aluminum platelets. In total, 270 ml of TiCl₄ are introduced into the fluidized bed over a period of 12 hours. The pigment shows metallic brightness with a reddish shimmer. A drawdown from this product has the CIELAB color coordinates $L^* = 107.1$, $a^* = 2.2$ and $b^* = 7.6$.

Following the TiO₂ coating, a 200 l/h stream of nitrogen laden with iron pentacarbonyl vapor by passage through an Fe(CO). filled saturating flask thermostated at 50° C. is blown through a nozzle into the furnace. The iron carbonyl reacts with the oxygen present therein to give iron oxide (hematite) and carbon dioxide. Under the chosen reaction conditions, the $Fe_2O_3$ formed settles out spontaneously in film form on the TiO₂ coated aluminum platelets. In total, 10 ml of Fe(CO)₅ are introduced into the fluidized bed over a period of 0.5 hours. A drawdown produced from a pigment sample shows high metallic brightness with a deep red shimmer and the CIELAB color coordinates $L^* = 102.8$; $a^* = 5.8$; $b^* = 8.9$.

EXAMPLE 4

The fluidized bed reactor is charged with a mixture of 150 g of commercial aluminum pigment having a BET surface area of 1.5 m²/g and a median particle diameter of 60 lm (90% of the particles being between 35 and 90 lm) and 150 g of commercial aluminum pigment having a BET surface area of 4.5 m²/g and a median particle diameter of 20 lm (90% of the particles being between 6 and 35 lm). The pigment is fluidized and homogenized by blowing 150 l/h of nitrogen and 180 l/h of air in at the lower opening of the cone. The air stream is passed through hot water at 50° C. The internal temperature of the fluidized bed is raised to 195°–200° C. by means of the IR radiators. Once this temperature range has been reached, a 200 l/h nitrogen stream, which is beforehand passed through hot water at 50° C., is used to introduce water vapor into the reactor, and the fluidizing gas stream is loaded with titanium chloride vapor by passage through a TiCl₄ filled saturating flask thermostated at 50° C. Under the chosen reaction conditions, the titanium dioxide formed settles out spontaneously in film form on the aluminum platelets. In total, 130 ml of TiCl₄ are introduced into the fluidized bed over a period of 7 hours. The pigment has a dark blue color. A drawdown produced from a pigment sample as described in Example 1 shows high metallic brightness and a deep blue shimmer.

EXAMPLE 5

25 g of the blue interference pigment produced as described in Example 4 are introduced into a 250 ml quartz rotating flask with built-in 0.5 cm wide trip strips and heated under nitrogen to 600° C. while the flask is turned. Dried NH₃ gas is then passed over the TiO₂ coated Al pigment at a rate of 30 l/h for 60 minutes. This is followed by 3 hours of cooling under a stream of nitrogen.

The product has a deep blue color with a slight reddish tinge. Micrographs show that the pigment has retained its platelet shape. X-rayographs reveal TiN and TiO (not distinguishable). Analysis indicates a 1% by weight level of $N^{3-}$.

We claim:

1. A metallically bright reflection pigment consisting of a substrate of plateletlike aluminum and a coating of titanium dioxide.

2. A metallically bright reflection pigment consisting of a substrate of plateletlike aluminum, a coating of titanium dioxide and an oxide of titanium where the titanium is in an oxidation state $<4$.

3. A metallically bright reflection pigment consisting of a substrate of plateletlike aluminum and a coating of titanium dioxide and a member selected from the group consisting of titanium nitride or titanium oxynitride.

4. A metallically bright reflection pigment consisting of a substrate of plateletlike aluminum, a coating of titanium dioxide and a coating of a different metal oxide.

5. A reflection pigment as defined in claim 4, wherein the metal oxide is iron oxide.

6. A process for preparing a metallically bright reflection pigment consisting essentially of plateletlike aluminum and a coating of titanium dioxide comprising passing $TiCl_4$ vapor at above 100° C. together with water vapor into a fluidized bed of plateletlike aluminum suspended with an inert carrier gas, with the proviso that the volume of the $TiCl_4$ vapor, based on the volume of the other gases and vapors introduced into the fluidized bed, does not exceed 5% by volume.

7. A process for preparing the reflection pigment defined in claim 6, which comprises passing $TiCl_4$ vapor at above 100° C. together with water vapor into a fluidized bed of plateletlike aluminum suspended with an inert carrier gas, with the proviso that the volume of the $TiCl_4$ vapor, based on the volume of the other gases and vapors introduced into the fluidized bed, does not exceed 5% by volume, and subsequently performing a treatment with a reducing gas at from 400° to 900° C.

8. A process for preparing the reflection pigment defined in claim 6, which comprises passing $TiCl_4$ vapor at above 100° C. together with water vapor into a fluidized bed of plateletlike aluminum suspended with an inert carrier gas, with the proviso that the volume of the $TiCl_4$ vapor, based on the volume of the other gases and vapors introduced into the fluidized bed, does not exceed 5% by volume, and subsequently performing a treatment with ammonia at from 400° to 900° C.

9. A process for preparing the reflection pigment defined in claim 6, which comprises passing $TiCl_4$ vapor at about 100° C. together with water vapor into a fluidized bed of plateletlike aluminum suspended with an inert carrier gas, with the proviso that the volume of the $TiCl_4$ vapor, based on the volume of the other gases and vapors introduced into the fluidized bed, does not exceed 5% by volume, and subsequently introducing vaporized iron pentacarbonyl into a fluidized bed of titanium oxide coated reflection pigment suspended with an inert carrier gas and oxidizing at above 150° C., with the proviso that the amount of iron pentacarbonyl introduced into the fluidized bed does not exceed 5% by volume, based on the total of gases introduced into the fluidized bed.

* * * * *

UNITED STATES PATENT AND TRADEMARK OFFICE
CERTIFICATE OF CORRECTION

PATENT NO. : 4,978,394
DATED : December 18, 1990
INVENTOR(S) : Werner OSTERTAG et al.

It is certified that error appears in the above-identified patent and that said Letters Patent is hereby corrected as shown below:

IN THE CLAIMS

Claim 9, Line 3:

"about" should read --above--

Signed and Sealed this

First Day of December, 1992

*Attest:*

DOUGLAS B. COMER

*Attesting Officer*      *Acting Commissioner of Patents and Trademarks*